United States Patent [19]

Miesch

[11] Patent Number: 4,956,377

[45] Date of Patent: Sep. 11, 1990

[54] USE OF BUTYL-4-DIPHENYL-1,2-PYRAZOLIDINE-DIONE-3,5 AS AN ANTIVIRAL AGENT IN HUMANS AND ANIMALS

[76] Inventor: Jean-Olivier Miesch, 2, place Jeanne d'Arc, Rambouillet, France

[21] Appl. No.: 482,587

[22] Filed: Feb. 21, 1990

Related U.S. Application Data

[63] Continuation-in-part of Ser. No. 344,523, Apr. 25, 1989, abandoned, which is a continuation of Ser. No. 33,821, Apr. 3, 1987, abandoned.

[51] Int. Cl.$^5$ ................................................ A61K 415
[52] U.S. Cl. .................................................. 514/404
[58] Field of Search ........................................ 514/404

[56] References Cited

PUBLICATIONS

Chemical Abstracts 70:104872x (1969).

*Primary Examiner*—Jerome D. Goldberg
*Attorney, Agent, or Firm*—Browdy and Neimark

[57] ABSTRACT

Viral infections, particularly retroviral infections such as infections with human immunodeficiency virus (HIV), can be treated wtih butyl-4-diphenyl-1,2,-pyrazolidine-dione, 3,5 (phenylbutazone).

6 Claims, No Drawings

USE OF BUTYL-4-DIPHENYL-1,2-PYRAZOLIDINE-DIONE-3,5 AS AN ANTIVIRAL AGENT IN HUMANS AND ANIMALS

This application is a continuation-in-part of Ser. No. 07/344,523, filed Apr. 25, 1989, now abandoned, which is itself a continuation application of U.S. Ser. No. 07/033,821 filed Apr. 3, 1987 and abandoned.

BACKGROUND OF THE INVENTION

The subject matter of the present invention is a new therapeutic use for a known medicine.

PRIOR ART

French Patent No. 983,378 (GEIGY) mentions that butyl-4-diphenyl-1,2-pyrazolidine-dione-3,5, is well known as an analgesic and antipyretic.

This product, which belongs to the class of non-steroidal anti-inflammatories and which is sold in composition form including a pharmaceutically acceptable carrier, has enjoyed great worldwide success, but the fear of undesirable side effects has led the ministry with responsibility for Public Health to limit its use to certain rheumatological ailments and to take off the market patent medicines in injectable form.

SUMMARY OF THE INVENTION

It has now been discovered according to the present invention that this same chemical product, i.e. butyl-4-diphenyl-1,2 pyrazolidine-dione-3,5, is an outstanding antiviral agent against diverse viral ailments caused by retroviruses such as HIV, and that it also has a considerable effect on certain viral diseases with DNA as their nucleic acid, such as herpes, possibly going as far as a total cure with "restitutio ad integrum".

DETAILED DESCRIPTION OF THE INVENTION

This product has shown itself to be effective in this new therapeutic application against ailments such as AIDS (acquired immunodeficiency syndrome) in all its clinical forms, including the most severe, as well as meningo-encephalitis, measles, rubella, mumps even in the form of parotiditis, oophoritis, orchitis or pancreatitis, viral hepatitis A, viral hepatitis B, legionellosis, yellow fever, rabies in humans, tropical meningo-encephalitis, haemorrhagic fevers, Sindbis virus, dengue, LCM arenavirus, Lassa fever, benign reoviral digestive and respiratory infections, paralytic diseases, especially acute anterior poliomyelitis and Echo virus epidemic meningitis, herpangina, Coxsackie hand, foot-and-mouth disease A and B, exanthematous herpangina, rhinoviral upper respiratory infections, acute respiratory infections such as colds, bronchitis, human, murine and avian coronavirus pneumonia, avian leucoses, Rous sarcoma, murine leukemia, myeloblastosis, mammary carcinoma, mammary tumours in mice, foot-and-mouth disease, Carre's disease in dogs, rabies, bovine or avian plague, epizootic diseases, silk-worm jaundice, tobacco mosaic virus, turnip yellow mosaic virus, potato virus X, and the ornamental tulip streak virus.

It is also effective against smallpox, cowpox, chicken pox, herpes zoster, Epstein-Barr disease, Guillain-Barre-Strohe syndrome, adenoviral infections, myxomatosis in rabbits, herpes simplex and herpes in animals, animal adenoviruses, cytomegalovirus and psittacosis in birds.

In the new application according to the invention, said active product can be used in the form of suppositories, tablets and injections with one dose of the order of 10 mg per kilo of the patient's body weight per day, that is to say a dose a long way from the lethal dose, which is 4 g per day.

The slow metabolism of said product, whose affinity for plasma proteins is particularly high, and the very slow excretion of the product (the plasma half life of the product being of the order of 72 hours, which is very long) enable the effect of the medicine to be prolonged, even after absorption by the organism of a single dose.

The patients are generally relieved within a relatively short period of time and treatment can continue with the dose being regularly decreased for a period of 5 to 7 days, finishing on the seventh day.

The product, which has also been successfully tested for its preventative effects, especially with regard to influenza, in isolation, in the worst conditions of epidemic indiscriminate mingling, did not give rise to any relapse, and the contra-indications are exceptional.

As the product has a sodium retentive effect, an aggressive effect on the gastric mucous in the case of prolonged treatment and an aggressive effect on the renal, hepatic and blood-forming cells, it is advisable to observe a certain number of precautions, when it is used against viral disorders.

If used in association with anti-vitamin K, it is advisable frequently to monitor coagulability to adapt the posology to the presence of anticoagulants; when treatment is prolonged, it is desirable to carry out renal and hepatic assessments; if edema appears, it is recommended that a hyposodium treatment, or better still a totally sodium-free treatment, possibly substituting a dietary salt such as magnesium chloride; finally prudence is essential in the treatment of an old patient or a patient suffering from hypertension and if digestive problems appear during treatment by oral administration, it is advisable to substitute treatment by rectal or parenteral means.

Without wishing to be bound by any explanation of the treatment according to the invention, it can be supposed that, in the case of viral disorders with a virus with RNA nucleic acid, which constitute approximately 80% of all viral diseases, the phenyl-NH radicals of the active product react with the enolic form of the uracil derived from the pyrimidine included, with the ribose and a phosphate, in the constitution of the riboncleic acid to destroy it.

The mode of action against viruses with DNA nucleic acid is different, the destruction being effected, as a function of the pH, by breaking the pyrimidine ring of the aryl chain thymine.

DESCRIPTION OF THE PREFERRED EMBODIMENT

The present invention will now be illustrated with the aid of a number of clinical observations, which examples are for purposes of illustration only and are non-limiting.

EXAMPLE 1

Patient No. 1, a 34-year old male, tested sero-positive for AIDS antibodies on Nov. 3, 1986, according to the ELISA immunofluorescence test. This patient was treated with orally administered phenylbutazone for seven days at 600 mmgr daily, then for the second week 400 mmgr daily, and for the third week with 200 mmgr daily. The patient was examined at the end of each week in order to verify tolerance for the medication, which was found to be perfect.

The hematology reports before and after phenylbutazone treatment are shown in Table 1.

TABLE 1

|  | Leucocytes | Total Lymphocytes | T4 | T8 | T4/T8 |
|---|---|---|---|---|---|
| Prior to Treatment | 5,300 | 2,070 | 497 | 1,242 | 0.40 |
| 2 Mos. Aft. Treatment | 6,000 | 2,280 | 593 | 1,231 | 0.48 |

The subpopulation of the patient's lymphocytes was absolutely normal following the phenylbutazone treatment. The patient's prognosis is excellent.

EXAMPLE 2

Patient No. 2, a 33 year old male, tested sero-positive for AIDS antibodies in April of 1986. When the patient was examined in August of 1987, he had Kaposi's sarcoma over much of his skin, and had been treated with interferon for eight months. The patient was treated with 600 mmgr of phenylbutazone daily for the first week, then with 400 mmgr phenylbutazone daily for the second week, then with 200 mmgr phenylbutazone daily for the third week. The patient was examined at the end of each week. He showed a good tolerance for the phenylbutazone except for the end of the third week, when a rash erupted which was rapidly treated with polaramine.

At the end of the phenylbutazone treatment regimen, the subpopulation of lymphocytes was normal.

The hematology reports before and after phenylbutazone treatment are shown in Table 2.

TABLE 2

|  | Leucocytes | Total Lymphocytes | T4 | T8 | T4/T8 |
|---|---|---|---|---|---|
| Prior to Treatment | 3,800 | 1,400 | 640 | 448 | 1.43 |
| 1 Mo. Aft. Beginning Treatment | 3,700 | 1,620 | 44 | 33 | 1.33 |

EXAMPLE 3

Patient No. 3, a 40 year old male, tested sero-positive for HIV in December, 1986, and was first evaluated for phenylbutazone treatment in December, 1987. The sero-positive test for HIV was confirmed with Western-blot analysis. A hemogram was taken on Sept. 28, 1987, and treatment was conducted by administering 600 mmgr daily of phenylbutazone for the first week, 400 mmgr daily for the second week, and 200 mmgr daily for the third week. The patient was reviewed at the end of treatment in December 1987. The patient had gained three kilograms, sleep had returned to normal, and the improvement in the general state of health was notable. There was a great elevation in the T4 lymphocytes and the T4/T8 ratio was from 0.41–0.49. At a later hematologic examination in February of 1988, the T4/T8 ratio remained unchanged and the beta-2-microglobulin was increased to 3.16. The conclusion reached was that the clinical recovery was obtained and was confirmed by the hematologic tests.

The hematology reports before and after treatment are shown in Table 3.

TABLE 3

|  | Leucocytes | Total Lymphocytes | T4 | T8 | T4/T8 |
|---|---|---|---|---|---|
| Prior to Treatment | 8,600 | 2,600 | 454 | 1,115 | 0.41 |
| 2 Mos. Aft. Treatment | 7,900 | 3,318 | 796 | 1,262 | 0.49 |

EXAMPLE 4

Patient No. 4 had tested sero-positive for HIV since June, 1986, and treatment commenced in December of 1987. Treatment was administered in the form of 600 mmgr phenylbutazone daily for the first week, 400 mmgr phenylbutazone daily for the second week, and 200 mmgr daily for the third week. The patient was examined at the end of each week. Since the patient was already infected with Hepatitis B virus,m there was still a certain degree of hepatic toxicity. However, in spite of this, the patient stated that he felt better.

The hematology reports before and after treatment are shown in Table 4.

TABLE 4

|  | Leucocytes | Total Lymphocytes | T4 | T8 | T4/T8 |
|---|---|---|---|---|---|
| Prior to Treatment | 5,500 | 2,475 | 347 | 1,262 | 0.27 |
| 1 Mo. Aft. Treatment | 4,300 | 1,290 | 413 | 542 | 0.76 |

EXAMPLE 5

Patient No. 5 had tested sero-positive for HIV in May, 1986, and then in July, 1986. His condition had not improved, and treatment was commenced in September, 1987, of a regimen of 600 mmgr phenylbutazone daily for the first week, 400 mmgr phenylbutazone daily for the second week, and 200 mgr phenylbutazone daily for the third week.

The patient reported that he was less fatigued than prior to treatment and had regained his appetite and had gained about one kilogram of weight.

The results of hematologic examinations before and after treatment are shown in Table 5.

TABLE 5

|  | Leucocytes | Total Lymphocytes | T4 | T8 | T4/T8 |
|---|---|---|---|---|---|
| Prior to Treatment | 5,500 | 2,475 | 347 | 1,262 | 0.27 |
| 1 Mo. Aft. Beginning Treatment | 4,300 | — | 413 | 542 | 0.76 |
| 7 Mos. Aft. Beginning Treatment | 6,600 | 2,442 | 659 | 1,197 | 0.55 |

EXAMPLE 6

Patient No. 6, a 43 year old male who was suffering from AIDS, had been treated with AZT and found that this medication aggravated his symptoms, particularly his lack of concentration and digestive problems. Additionally, he was afflicted with insomnia and slight anorexia. He exhibited a generalized enlargement of the lymph glands and cutaneous Kaposi's sarcoma.

Treatment was administered at the rate of 600 mmgr phenylbutazone daily for the first week, 400 mmgr phenylbutazone daily for the second week, and 200 mmgr phenylbutazone daily for the third week.

After treatment, there was a total reduction of the adenopathy, as well as a disappearance of sensitivity in the extremities. The patient noted no special reaction for the first two days of treatment, but the next two days he had the impression of being chilled in the back, and there was a total disappearance of his fever and headaches. The last two days, his physical condition had settled down. After treatment, his general condition was very good, and the disappearance of the clinical signs of morbidity was confirmed by hematology.

The results of the hematology before and after treatment are shown in Table 6.

TABLE 6

|  | Leucocytes | Total Lymphocytes | T4 | T8 | T4/T8 |
| --- | --- | --- | --- | --- | --- |
| Prior to Treatment | 3,200 | 1,290 | 250 | 790 | 0.3 |
| 1 Mo. Aft. Beginning Treatment | 3,800 | 1,611 | 291 | 985 | 0.3 |

EXAMPLE 7

Patient No. 7, a 39 year old male, had previously been treated with AZT. This medication appeared to aggravate his symptoms, particularly his lack of concentration and digestive problems. The diagnosis of AIDS was made in January, 1986, and confirmed by a second test in June, 1987, by the three specific antigens, (p24, GP41, and GP120/160). This patient suffered from a loss of appetite with loss of weight, debility, and loss of memory, and generalized adenopathy over all of the body.

Treatment was commenced with phenylbutazone in dosages of 600 mmgr daily for the first week, 400 mmgr daily for the second week, and 200 mmgr daily for the third week.

After one week of treatment, the patient's overall state appeared good, and there was improvement in the adenopathies. After two weeks of treatment, the patient's general state was very good, and the disappearance of clinical signs of morbidity was confirmed. After three weeks of treatment, there was a clinical and biological confirmation of cure, and there was an absence of p24 viral antigens.

The hematologies before and after treatment are shown in Table 7.

TABLE 7

|  | Leucocytes | Total Lymphocytes | T4 | T8 | T4/T8 |
| --- | --- | --- | --- | --- | --- |
| Prior to Treatment | 6,100 | 2,900 | 261 | 848 | 0.31 |
| 1 ¼ Mos. Aft. Beginning Treatment | 5,876 | 1,645 | 280 | 1,044 | 0.28 |

EXAMPLE 8

Patient No. 8, a 30 year old female, tested positive for HIV infection by ELISA and Western Blot analyses. She suffered from persistent adenopathies.

The patient was treated with 200 mmgr phenylbutazone administered three times a day for the first week, two times a day for the second week, and once a day for the third week.

After treatment, there was a complete disappearance of the adenopathies, and her general state of health was very good.

The hematologies before and after treatment are shown in Table 8.

TABLE 8

|  | Leucocytes | Total Lymphocytes | T4 | T8 | T4/T8 |
| --- | --- | --- | --- | --- | --- |
| Prior to Treatment | 4,400 | 1,628 | 570 | 521 | 1.09 |
| 1 Mo. Aft. Beginning Treatment | 5,000 | 1,500 | 630 | 480 | 1.31 |
| 4 Mos. Aft. Beginning Treatment | 4,200 | 1,932 | 773 | 541 | 1.43 |

EXAMPLE 9

Patient No. 9, a 31 year old male, had tested positive for HIV infection by both ELISA and Western blot analyses. Although he had been successfully treated for bronchitis, there was still a certain debility in the patient.

Treatment with 200 mmgr phenylbutazone was administered three times daily for the first week, twice daily for the second week, and once daily for the third week.

Two months after treatment, except for the immunoglobulins, which did not change, the biological indications of AIDS continued to improve, and the patient's general good state remained. The patient's appetite increased, he had gained three kilograms, and the prognosis is very favorable.

Results of hematologies conducted before and after treatment are shown in Table 9.

TABLE 9

|  | Leucocytes | Total Lymphocytes | T4 | T8 | T4/T8 |
| --- | --- | --- | --- | --- | --- |
| Prior to Treatment | 4,400 | 1,628 | 570 | 521 | 1.09 |
| 1 Mo. Aft. Beginning Treatment | 5,000 | 1,500 | 630 | 480 | 1.31 |

EXAMPLE 10

Patient No. 10, a 23 year old male, had been treated several times for intoxication, and had been contaminated with HIV since 1986, when he tested sero-positive for HIV by ELISA and Western Blot. He had been treated for facial boils with bleomycin cream for two months.

Treatment with 200 mmgr phenylbutazone was administered three times daily for the first week, twice daily for the second week, and once daily for the third week.

One month after treatment all of the biological parameters were completely normal. The patient feels very good, there are no clinical symptoms, and the prognosis is very favorable.

The hematologies before and one month after treatment are shown in Table 10.

TABLE 10

| | Leucocytes | Total Lymphocytes | T4 | T8 | T4/T8 |
|---|---|---|---|---|---|
| Prior to Treatment | 6,600 | 1,980 | 515 | 772 | 0.67 |
| 1 Mo. Aft. Treatment | 9,200 | 1,932 | 560 | 753 | 0.74 |

EXAMPLE 11

Patient No. 11, a 33 year old male, was asymptomatic, yet tested seropositive for HIV by both ELISA and Western blot analyses. Treatment with 200 mmgr phenylbutazone was administered three times daily for the first week twice daily for the second week, and once daily for the third week.

Two months after treatment, the patient remained asymptomatic, and there was no antigen or antibody to HIV present in the patient's serum. All of the biological criteria were improved to the point of absolutely normal indications. The general state of the patient is excellent, and there appears to be a complete biological and clinical cure.

The hematologies before and after treatment are shown in Table 11.

TABLE 11

| | Leucocytes | Total Lymphocytes | T4 | T8 | T4/T8 |
|---|---|---|---|---|---|
| Prior to Treatment | 6,100 | 3,355 | 1,174 | 738 | 1.59 |
| 1 Mo. Aft. Treatment | 7,000 | 2,800 | 840 | 672 | 1.25 |

EXAMPLE 12

Patient No. 12, a 27 year old male, tested HIV positive. The patient had moderate dysphagia, a dry cough, debility, white spots on the skin but without leukoplasia. There was a suspicion of Kaposi's sarcoma on the abdomen.

Treatment with 200 mmgr phenylbutazone was administered three times daily for the first week, two times daily for the second week, and once daily for the third week.

After treatment with phenylbutazone, the beginning of polyadenopathy had completely disappeared, as well as buccal mycosis. The general state of the patient is good, and the appetite and weight have been conserved. There is no further manifestation of opportunistic infections.

The hematologies before and after treatment are shown in Table 12.

TABLE 12

| | Leucocytes | Total Lymphocytes | T4 | T8 | T4/T8 |
|---|---|---|---|---|---|
| Prior to Treatment | 6,800 | 2,724 | — | — | — |
| 1 Mo. Aft. Treatment | 6,700 | 2,948 | 531 | 1,680 | 0.32 |
| 4 Mos. Aft. Beginning Treatment | 5,400 | 1,890 | 378 | 1,040 | 0.36 |

EXAMPLE 13

Patient No. 13, a 30 year old female, tested HIV positive when she was tested in connection with an ovarian cyst. She was observed without treatment for ten months.

Treatment with 200 mmgr phenylbutazone was administered three times daily for the first week, twice daily for the second week, and once daily for the third week.

Two months after treatment, all of the biological parameters were improved, notably the augmentation of the T4 lymphocytes. The patient felt very good, and the clinical symptoms were nonexistent. The prognosis is very favorable.

The hematologies before and after treatment are shown in Table 13.

TABLE 13

| | Leucocytes | Total Lymphocytes | T4 | T8 | T4/T8 |
|---|---|---|---|---|---|
| Prior Treatment | 4,700 | 1,880 | 278 | 972 | 0.29 |
| 2 Mos. Aft. Treatment | 6,400 | 2,048 | 410 | 1,106 | 0.32 |

EXAMPLE 14

Patient No. 14, a 28 year old male, tested seropositive for HIV during a preliminary examination prior to donating blood. The patient had been treated with AZT. Although the patient was seropositive for HIV, he was asymptomatic.

Treatment with 200 mmgr phenylbutazone was administered three times daily for the first week, twice daily for the second week, and once daily for the third week.

One month after commencement of treatment, the severe immunodeficiency the patient had exhibited was gone except for a certain degree of agranulocytosis. Treatment for this condition was proposed.

The hematologies before and after treatment are shown in Table 14.

TABLE 14

| | Leucocytes | Total Lymphocytes | T4 | T8 | T4/T8 |
|---|---|---|---|---|---|
| Prior to Treatment | 3,700 | 1,332 | 67 | 892 | 0.07 |
| 1 Mo. Aft. Treatment | 2,600 | 1,092 | 44 | 710 | 0.06 |

When taken orally, phenylbutazone easily crosses the meningeal barrier.

In cases of uncertainty between the risk of simple inflammation and the viral risk of a virus with deteriorating, or even fatal, development, there is no contraindication, in view of the above clinical results, against prescribing an anti-infectious therapy based on butyl-4-diphenyl-1,2-pyrazolidine-dione-3,5.

In serious cases, in which microbial superinfection is suspected, the product in question can and must be associated with conventional antibiotherapy, the results proving that there is potentiation exhibiting only advantages and no disadvantages from the point of view of treatment.

It is particularly interesting to note that oral administration of this product brings about a systematic sweeping of any viral disorder, whatever its location in the organism, which is particularly important in cases of glandular or other metastasic disorders, when the irreversible damage of any glandular disorder and the serious consequences which can result therefrom are known.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for treating a patient infected with human immuno deficiency virus comprising administering to said patient an effective amount of a composition consisting essentially of butyl-4-diphenyl-1, 2-pyrazolidine-dione-3,5.

2. The method according to claim 1, wherein said patient is suffering from acquired immune deficiency syndrome.

3. The method according to claim 1 wherein said butyl-4-diphenyl-1,2-pyrazolidine-dione-3,5 is administered in amounts of about 10 mg per kilogram of body weight per day.

4. The method according to claim 3 wherein said butyl-4-diphenyl-1,2-pyrazolidine-dione-3,5 is administered for up to three weeks.

5. The method according to claim 1 wherein said butyl-4-diphenyl-1,2-pyrazolidine-dione-3,5 is administered in an amount of about 600 mmgr per day for one week, about 400 mmgr per day for one week, and about 200 mmgr per day for one week.

6. The method according to claim 1 wherein said butyl-4-diphenyl-1,2-pyrazolidine-dione-3,5 is administered to an adult patient at an initial dosage rate of about 500–600 mg for the first day and then the dosage rate is progressively reduced, and administration is terminated after administration thereof at a lower dosage rate of 200–400 mg per day for a plurality of days.

* * * * *